United States Patent
Nieva Escandon et al.

(10) Patent No.: US 8,110,545 B2
(45) Date of Patent: Feb. 7, 2012

(54) NON-PROTEOLYSABLE OLIGOPEPTIDES THAT INHIBIT GLYCOPROTEIN GP41 OF THE AIDS VIRUS

(75) Inventors: Jose Luis Nieva Escandon, Vizcaya (ES); Maria Jose Gomara Elena, Vizcaya (ES); Maier Lorizate Nogales, Vizcaya (ES); Nerea Huarte Arrayago, Vizcaya (ES); Ismael Mingarro Munoz, Valencia (ES); Enrique Perez Paya, Valencia (ES)

(73) Assignees: Universidad Del Pais Vasco, Leioa, (Vizcaya) (ES); Universidad de Valencia, Valencia (ES)

( * ) Notice: Subject to any disclaimer, the term of this patent is extended or adjusted under 35 U.S.C. 154(b) by 634 days.

(21) Appl. No.: 12/159,645

(22) PCT Filed: Dec. 29, 2006

(86) PCT No.: PCT/ES2006/000726
§ 371 (c)(1),
(2), (4) Date: Oct. 17, 2008

(87) PCT Pub. No.: WO2007/077278
PCT Pub. Date: Jul. 12, 2007

(65) Prior Publication Data
US 2010/0197606 A1    Aug. 5, 2010

(30) Foreign Application Priority Data

Dec. 30, 2005    (ES) .................................. 200503259

(51) Int. Cl.
*A61P 31/18* (2006.01)
*A61K 38/08* (2006.01)

(52) U.S. Cl. ........................................ 514/4.1; 514/21.8

(58) Field of Classification Search ........................ None
See application file for complete search history.

(56) References Cited

U.S. PATENT DOCUMENTS

| 4,910,131 | A  | * | 3/1990  | Mellman et al. | ................... | 435/5   |
| 2002/0164732 | A1 | * | 11/2002 | Chopin et al.  | ................. | 435/183 |
| 2003/0233675 | A1 | * | 12/2003 | Cao et al.     | ..................... | 800/279 |

FOREIGN PATENT DOCUMENTS

| WO | 89/09785  | 10/1989 |
| WO | 03/104262 | 12/2003 |

OTHER PUBLICATIONS

Pritsker, M., et al. "A synthetic all D-amino acid peptide corresponding to the N-terminal sequence of HIV-1 gp41 recognizes the wild-type fusion peptide in the membrane and inhibits HIV-1 envelope glycoprotein-medicated cell fusion." *Proc. Natl. Acad. Sci. USA* (1998) pp. 7287-7292.

Gomara, M. J., et al. "Hexapeptides that interfere with HIV-1 fusion peptide activity in liposomes block GP41-mediated membrane fusion." *FEBS Letters* (2006) vol. 580, No. 11, pp. 2561-2566.

* cited by examiner

*Primary Examiner* — Cecilia J Tsang
*Assistant Examiner* — Ronald Niebauer
(74) *Attorney, Agent, or Firm* — Ladas Parry LLP (57) ABSTRACT

The invention relates to non-proteolysable oligopeptides that inhibit glycoprotein 41 of the AIDS virus. More specifically, the invention relates to the identification of oligopeptides, particularly hexapeptides, (D), (L) or mixed, preferably D-hexapeptides, which inhibit the binding of a retrovirus to a target cell, thereby providing novel therapies against infection from the human immunodeficiency virus (HIV). The invention also relates to the use of said D-hexapeptides in the form of single components or complex mixtures as prophylactic or therapeutic agents for retroviral infections, especially human immunodeficiency virus type 1 (HIV-1).

8 Claims, 5 Drawing Sheets

NON-PROTEOLYSABLE OLIGOPEPTIDES THAT INHIBIT GLYCOPROTEIN GP41 OF THE AIDS VIRUS

FIELD OF THE INVENTION

This invention may be included within the field of proteomics. It relates to the identification of oligopeptides which inhibit, in vitro, the fusion of a retrovirus with a target cell, providing new therapies against infection by the human immunodeficiency virus (HIV). Furthermore, this invention relates to the use of said oligopeptides, as single components or in complex mixtures, as prophylactic or therapeutic agents for retroviral infections, specially HIV type 1.

BACKGROUND OF THE INVENTION

The AIDS epidemic has experienced a quick growth in the past 25 years (estimated number of patients at the end of 2004: 39.4 million). The use of highly-active anti-retroviral therapies (HAART) has significantly increased the life expectancy of persons infected by HIV. However, long-term treatments have caused the selection of HAART-resistant virus variants. This situation has made it necessary to develop new compounds that may be effective in fighting said variants. The addition of the fusion inhibitor "enfuvirtide" (also known as Fuzeon, T-20 or DP178) to the arsenal of anti-HIV compounds has meant a great advance in the control of multi-resistant viruses (1-3).

Figure 1:
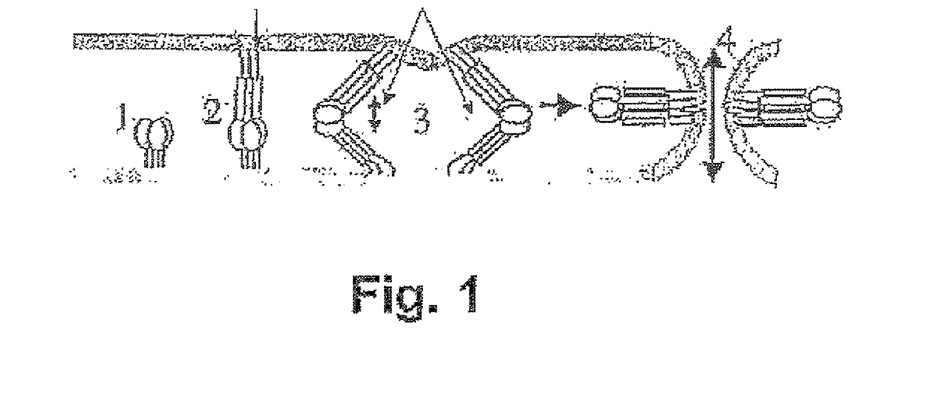
Figure 2:
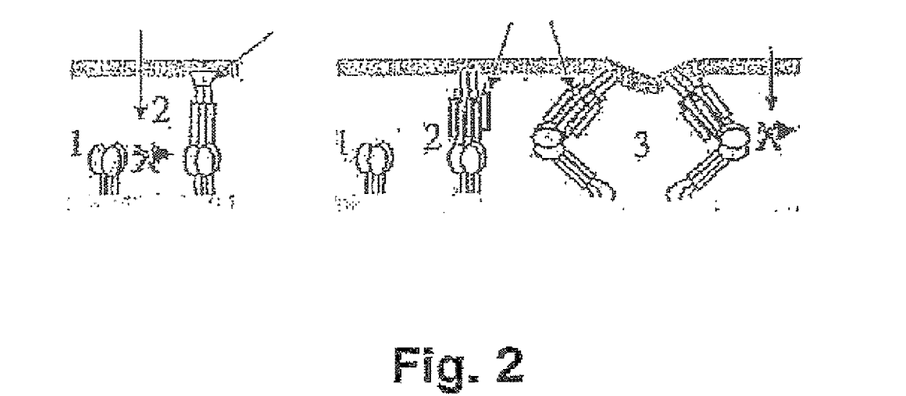

This compound acts on a key process of the infective cycle: the fusion of viral and cellular membranes promoted by viral coat glycoprotein gp120/41 (4). Its active principle is the T-20 peptide, which imitates a helicoidal sequence of gp41 that wraps in the hydrophobic grooves formed in the contact area between the helices of an imperfect trimeric coiled-coil. Wrapping is required in order to close a fork that clamps the membranes and causes the fusion thereof. T-20 competitively inhibits the closing process of the fork and, therefore, inhibits the fusion (FIG. 2).

However, the high production cost of "enfuvirtide" and the appearance of virus variants that are resistant to this compound have called into question its generalised use in anti-HIV therapy. Therefore, it is necessary to work in the development of new alternative compounds which are effective fusion inhibitors, have a lower cost and may be included within integrated strategies to control the disease. If these compounds act through a mechanism different from "enfuvirtide"'s, they could be used concertedly in the elimination of viruses which have developed resistance to HAART treatments. Moreover, they could represent an alternative to standard fusion inhibition therapies in cases of resistance to "enfuvirtide".

The amino-terminal sequence of fusogenic protein gp41 of HIV-1 is hydrophobic and highly conserved amongst the different strains, variants and clinical isolates (5). This is due to the fact that it is required in order for the protein to perform the fusogenic function (reviewed in 6). In accordance with its function, this sequence is called "fusion peptide" (hereinafter, FP). Its high degree of conservation and its functionality make this sequence a suitable therapeutic target for the development of anti-gp41 inhibitors. Previous data indicate that certain oligopeptides are capable of interfering with the fusogenic activity of gp41 (7), as well as with the interaction of synthetic FP with liposomes (8).

Patent application WO 03/104262 A2 discloses peptides designed to inhibit the fusion of protein gp41 of HIV with target cells, and patent application WO 2004/047730 A2 discloses a chemical compound with molecular weight between 200 and 1,200 Daltons, and logP between −2.0 to +5.5, which is capable of reciprocally acting with the hydrophobic cavity and blocking fusion formulation with the coiled coil of gp41.

But all these methods designed to prevent HIV infection and cure AIDS are still limited. Consequently, there is still the need to develop new viral inhibitors, specially inhibitors that are non-toxic or have an acceptably low toxicity.

There are various peptide synthesis methods that are distinguished by the physical state of the phase wherein said synthesis takes place, that is, in the liquid phase or the solid phase (see, for example, patent applications WO 2005/063791 A2, WO 2005/063792 A2 and WO 2005/063793 A2). In the solid phase, a first amino acid or peptide is bound to an insoluble support, such as a resin. Successive groups of amino acids or peptides are added until the desired peptide is obtained. Subsequently, said peptide is separated from the resin, isolated and identified.

But this invention relates to the synthesis and isolation of oligopeptides, not hydrolysable by cellular proteases, which interfere with FP, as potential new "fusion inhibitor" agents for HIV, and operate according to a mechanism that is substantially different from that of "enfuvirtide". The oligopeptides of this invention act by blocking the insertion of the FP in the target cell membrane and interfering with the self-assembly processes that take place on the surface thereof. On the contrary, "enfuvirtide" acts in a subsequent step, by preventing closing of the fork (see FIG. 2) once the virus and the host cell have come into contact.

DESCRIPTION OF THE INVENTION

Brief Description of the Invention

This invention discloses the identification of synthetic oligopeptides (hereinafter, oligopeptides of the invention) that have anti-gp41 activity, which have been developed on the basis of their capacity to block, in vitro, the activity of the fusion peptide, a sequence that is absolutely conserved amongst most HIV strains and clinical isolates.

Given the degree of conservation of the FP, the appearance of variants that are resistant to these compounds is expected to be quite remote.

Figure 3:
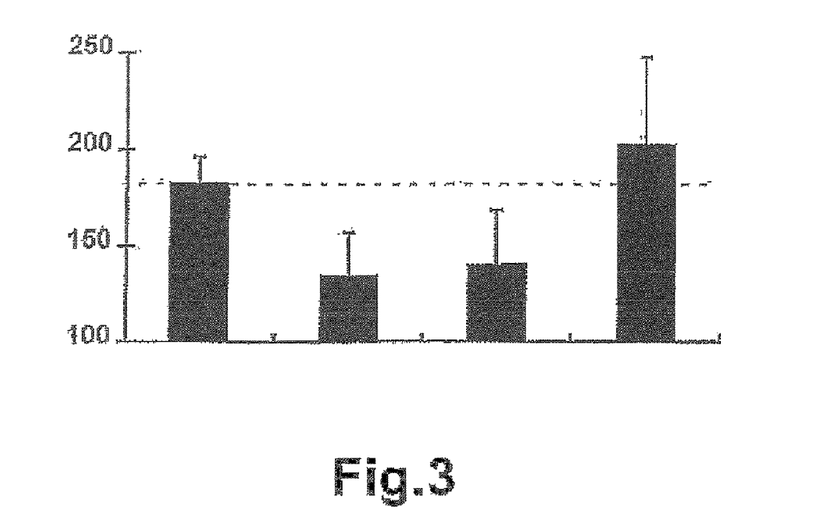
Figure 4:
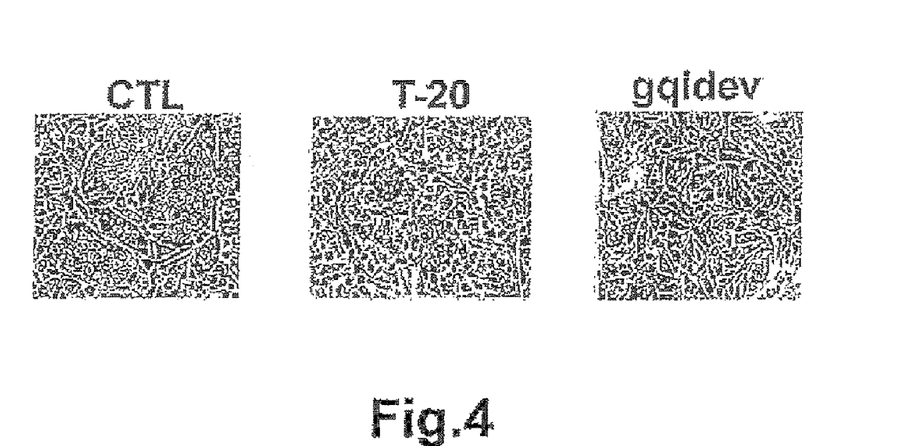
FIG. 4 Inhibitory effect of oligopeptide gqidev, identified by SEQ ID NO: 1 (5 µM micromolar) on the gp41 activity of HIV-1 (BH10 isolate: Gene Bank access number M15654) under the conditions described in the preceding figure. In the untreated cells (CTL), we can observe the formation of syncytia (multi-nucleated cells produced by the activity of gp41). As a positive inhibition control, cells treated with 20 nM of T-20 (enfuvirtide) are shown. The sample, in the sole presence of gqidev, was processed following the protocol described in the preceding figure. These two samples show a comparable inhibition of gp41.
Figure 5:
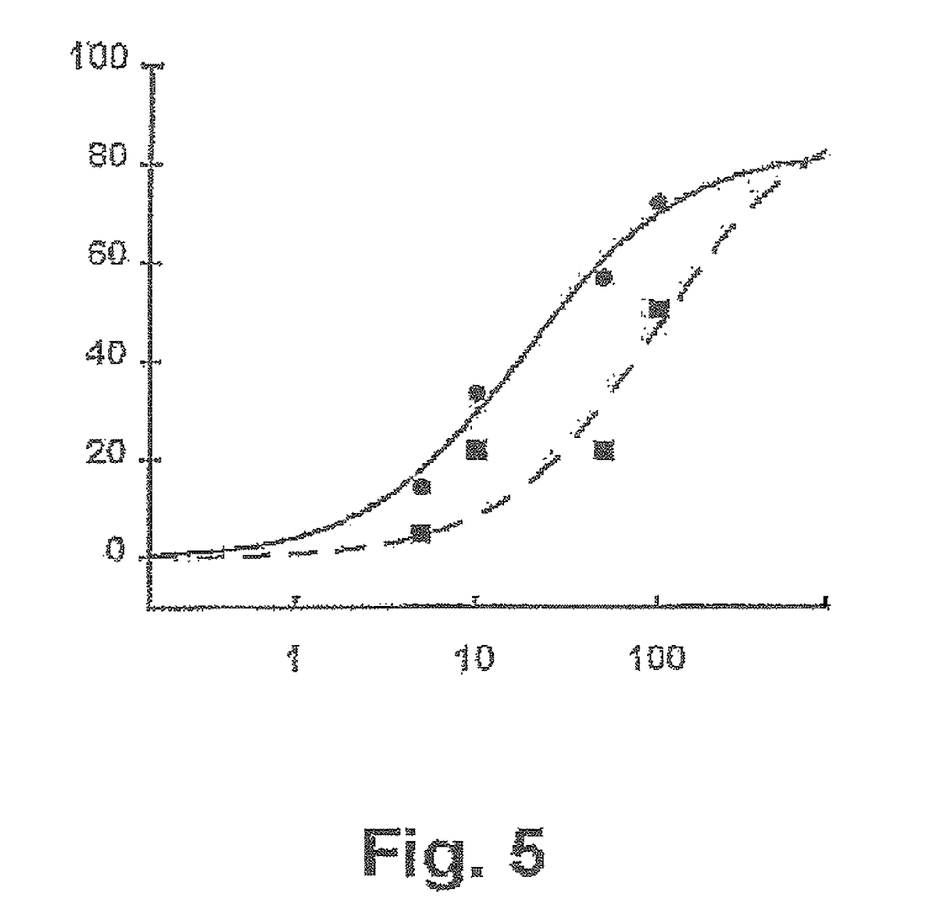
FIG. 5 Quantification of the inhibitory effect of oligopeptides gqidev, identified by SEQ ID NO: 1 (circles and broken line), and gqidqv, identified by SEQ ID NO: 2 (boxes and broken line), on the capacity of gp41 to induce cell fusion (formation of syncytia). The lines represent adjustments to hyperbolic-type functions. The assay, in the presence of increasing quantities of oligopeptides, was performed and quantified in accordance with the description of FIG. 3. 100% inhibition corresponds to the total absence of nuclei in syncytial plates, and 0% to the number of nuclei in said plates in control samples not treated with the oligopeptides.

This invention comprises the synthesis and identification of oligopeptides as inhibitors of the fusogenic activity of gp41. These oligopeptides have been identified by means of a position tracking process in peptide libraries. As a preferred embodiment of the invention, the oligopeptide identification process was focused on the characterisation of hexapeptides, since the structure of the latter may be used more effectively, leading to the conclusion that all the D-hexapeptides that result from substituting position 5 with any of the (D) stereoisomers of the known amino acids, had a similar inhibitory activity against HIV. The activity of said oligopeptides is manifested in the inhibition of interaction of the FP sequence with membranes and as the inhibition of cell fusion capacity when gp120/41 is expressed on the surface of the cells under culture (FIGS. 3-5). It was demonstrated that the oligopeptides of the invention have characteristic amino acid sequences, since a related hexapeptide with a similar sequence, such as, for example, the hexapeptide characterised in that it has sequence SEQ ID NO: 3, used as a negative control, with a single chemically non-conservative change of an amino acid residue in position 2, does not exhibit anti-gp41 activity (FIG. 3. The use of the oligopeptides of the invention as fusion inhibitor compounds for HIV-1, which are useful in the fight against virus variants that are resistant to the treatments used as a therapy, is disclosed.

As cited in this invention, oligopeptides are understood to mean those peptides formed by ten amino acids or less.

DESCRIPTION OF THE FIGURES

FIG. 1 Functional cycle of gp41 and proposed action mechanisms. Activation of the surface protein (1) exposes the Fusion Peptide of gp41, which facilitates the insertion thereof in the cell membrane (2). Subsequently, the co-ordinated collapse of several proteins or closing of the fork (3) causes juxtaposition of the membranes, the mixing thereof and the opening of an aqueous connection between the virus and the cell (4).

FIG. 2 RIGHT: Fusion inhibition by blocking closing of the fork (T-20).

LEFT: Fusion inhibition by blocking the insertion of the fusion peptide (oligopeptide of the invention) in the cell membrane. The oligopeptides of the invention act as blocking agents of the activity of the fusion peptide and inhibit the membrane fusion induced by protein gp41 of the human immunodeficiency virus.

FIG. 3 Effect of different inhibitory oligopeptides identified by deconvolution of a peptide library (position tracking) on the activity of gp41. The effect has been measured as the inhibition of cell-cell fusion induced by gp41 of HIV-1 expressed in CHO cells, which takes place when they are mixed with CD4 receptor-expressing HeLa cells (BH10 isolate: Gene Bank access number M15654). The oligopeptide concentration was 5 µM and the temperature was 37° C. Incubation in the cell culture medium (GMEM-S supplemented with 1 mM sodium pyruvate and 0.4 mM methionine sulfoximine) was performed for 16 hours. The bars correspond to the number of nuclei in syncytial plates (fused cells with more than 4 nuclei) per field after this time. The means of 4 individual measurements plus the standard deviations are shown.

Y-axis (ordinates): number of nuclei in syncytial plates (fused cells with more than 4 nuclei).

X-axis (abscissas): from left to right, CTL (untreated cells), gqidev (oligopeptide identified by SEQ ID NO: 1), gqidqv (oligopeptide identified by SEQ ID NO: 2) and gpidqv (oligopeptide identified by SEQ ID NO: 3).

Y-axis (ordinates): percentage of inhibition.

X-axis (abscissas): oligopeptide (µM).

Step 1 (deprotection): 20% piperidine is introduced in DMF and the result is Fmoc.

Step 2 (amino acid coupling).

Step 5 (acetylation of the Nt end): acetic anhydride is introduced in DMF.

Step 6 (splitting of the resin).

MALDI-TOF mass spectrum of the purified peptide, with a theoretical molecular mass of 964.1 Da.

DETAILED DESCRIPTION OF THE INVENTION

Peptide Synthesis and Purification
Synthesis Method

The combinatorial peptide library and the individual peptides were synthesised using the solid-phase multiple peptide synthesis methodology and following the standard procedures with the base-labile N-(9-fluorenyl)methoxycarbonyl (Fmoc) group to protect the α-amino function. The principles of solid-phase synthesis were developed in order to provide a quick, simple and effective way to synthesise peptides and small proteins. The methodology used consists of partitioning the polymer resin that acts as solid support into small bags of semi-permeable polypropylene which allow for the flow of solvents, whilst the resin remains inside. This methodology makes it possible, within the same synthesis process, to synthesise as many peptides (or, in the case of libraries, peptide mixtures) as bags incorporated into the process. The peptides were synthesised on a polystyrene aminomethyl RAM resin (RAPP Polymere). This is a high-substitution resin, of 0.76 meq/g of resin, that is used for peptides. Using this resin, the carboxy-terminal (Ct) end of the peptides obtained is amidated. All the amino acids used (Novabiochem and SENN Chemicals) have the amino group protected by the Fmoc protection group and the lateral chains protected by different protection groups, depending on the chain's functionality. The triphenyl (Trt) protection group was used for the cysteine, histidine, asparagine and glutamine amino acids; the terc-butyl (t-Bu) group was used for the aspartic, glutamic, serine, threonine and tyrosine amino acids; the 2,2,5,7,8-Pentamethylchroman-6-sulfonyl (Pmc) was used for arginine; and the tert-butoxycarbonyl (BOC) group was used for lysine and tryptophan (Table 1).

Figure 6:
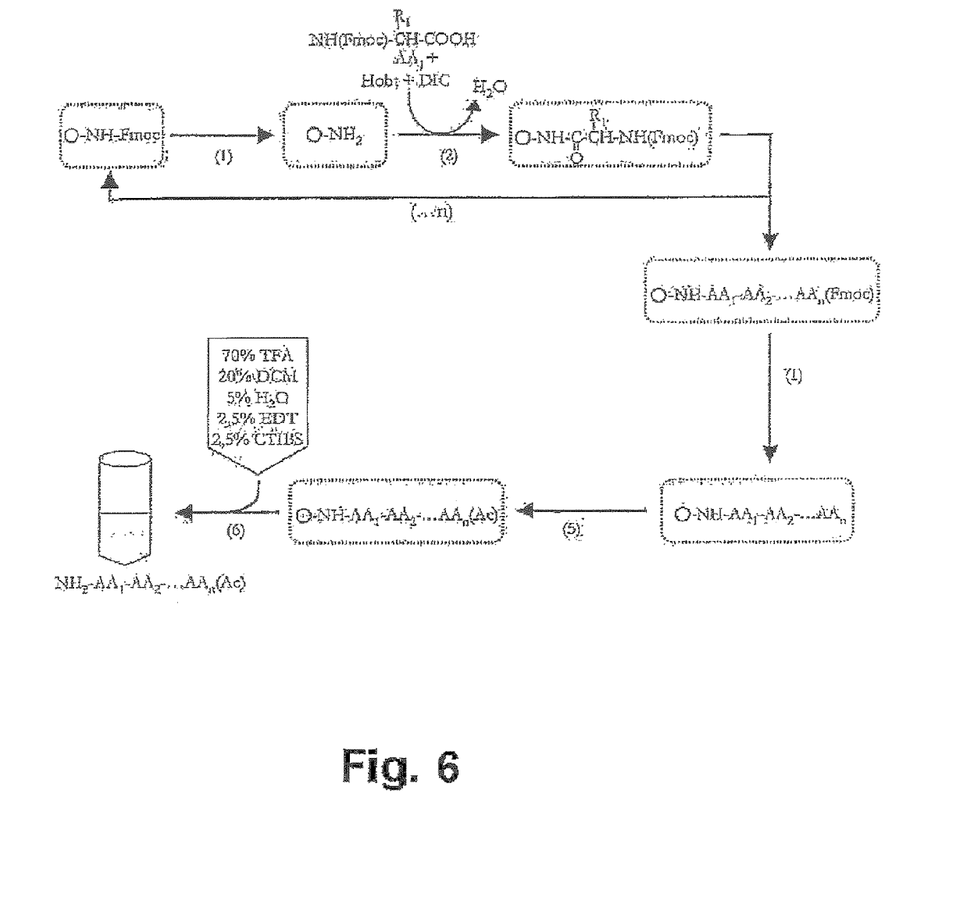
FIG. 6 Outline of the multiple oligopeptide synthesis method, which shows the steps performed to this end.

In oligopeptide synthesis, both the L stereoisomers (hereinafter, L-amino acids) and the D stereoisomers (hereinafter, D-amino acids) of natural amino acids are used. In this example, D-amino acids were used, and three oligopeptides, represented by sequences SEQ ID NO: 1, SEQ ID NO: 2 and SEQ ID NO: 3), were synthesised. The oligopeptide synthesis method is outlined in FIG. 6 and consists of successive deprotection cycles of the resin's amino group or the last coupled amino acid (by releasing the Fmoc protection group) and coupling of the next amino acid by activation of its carboxyl group (Stewart & Young, 1984; Baldwin et al., 1995). The protocol used consists of:

Deprotection of the amino group. 20% piperidine in dimethylformamide (DMF) was used, which breaks and releases the Fmoc group. It was performed twice, the first time for 5 min, when approximately 80% of the Fmoc group is released, and the second time in order to completely eliminate Fmoc.

Amino acid coupling. By mathematical calculation, the necessary quantity of amino acid was determined, taking into consideration a synthesis yield of 60%, and a 6-fold excess was used, dissolved in DMF. In order to favour the couplings, diisopropylcarbodiimide (DIC) and anhydrous 1-hydroxybenzotriazole (HOBt) were used. For every equivalent of amino acids, one equivalent of HOBt and two equivalents of DIC were used. DIC acts as a coupling agent, forming a ternary complex with the acid and the amine, and favouring the formation of the peptide bond. HOBt activates the amino acids' carboxyl end in the form of asymmetric esters. The couplings were performed for 1 h 30 min at ambient temperature under stirring.

1. Following each of the steps described above, the resin was subject to a series of washes:
   Three washes with DMF, which eliminate the Fmoc residues following the deprotection process or the coupling mixture residues.
   Three washes with isopropanol, which cause contraction of the resin in order to facilitate washing of the resin's interstitial gaps.
   Three washes with dichloromethane (DCM), which causes expansion of the resin, facilitating the following step (either deprotection, coupling or splitting of the peptide from the resin).

2. Each deprotection and coupling step was verified by the Kaiser test. This test is based on the reaction of ninhydrin with the free amino groups and is applied to a small aliquot of resin. In this way, the Fmoc group's deprotected amino acid or resin should produce an intense blue colour with the reagent. If the amino acid is proline, a brown colour is obtained. Following the coupling of an amino acid, or in the event of incomplete deprotection, the Kaiser test will be negative, resulting in a yellow colour. The Kaiser test is destructive; for this reason, it should be used with the minimum amount of resin. Furthermore, it is qualitative, such that it does not distinguish amongst different degrees of deprotection. For this reason, the deprotection was additionally confirmed by measuring the absorbance of the free Fmoc group at 290 nm (the molar extinction coefficient (c) is 4,950 $M^{-1}$ $cm^{-1}$). These first four steps are repeated depending on the number of amino acids of the peptide to be synthesised. In our example, they were repeated six times for each amino acid.

3. Acetylation of the amino-terminal group (Nt). Following the last coupling, the Fmoc group of the amino group was eliminated (step 1) and the free Nt end was acetylated with 20% acetic anhydride in DMF. The washes in step 3 were performed again.

4. Finally, complete deprotection of the amino acids' lateral chains and splitting of the resin were performed. The resin in each bag was separately extracted and placed in a plastic column. This was performed by treatment with a mixture of 70% trifluoroacetic acid (TFA), 20% dichloromethane (DCM), 5% water, 2.5% ethanedithiol (EDT), 2.5% chlorotriisobutylsilane (CTIBS) at ambient temperature for 4 hours. Water, ethanedithiol and chlorotriisobutylsilane act as trappers of the free radicals obtained in the deprotection of the groups that protect the amino acids' lateral chains.

5. Precipitation and lyophilisation of the peptide. Following filtering of the resin and washing with TFA, the split peptides were precipitated in cold t-butylmethylether for at least 12 h at −80° C., centrifuged at 3,000 rpm for 15 min (SANYO MSE centrifuge), dissolved in acetic acid and lyophilised. Following this first lyophilisation, the peptides were reconstituted; to this end, they were dissolved in a water: acetonitrile solution (H20:CH3CN, 80:20 proportion, respectively) and once again lyophilised.

Purification of the Individual Peptides

Figure 7:
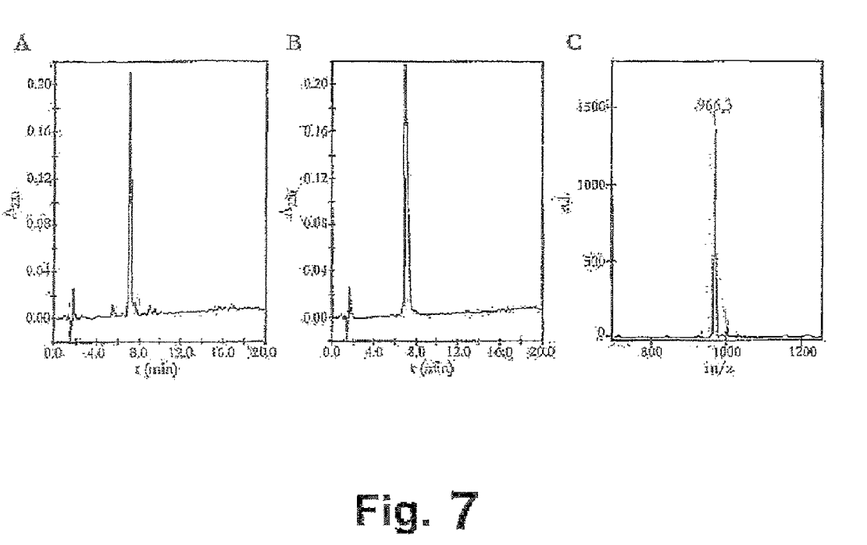
FIG. 7 HPLC chromatograms of an example oligopeptide:
A. prior to purification.
B. following purification.
C. using a linear gradient of CH3CN from 30% to 40% in H20 for 15 min.

Following the synthesis, a purification and quality analysis process was performed, which is reflected in FIG. 7 with an example.

The chromatographic profile of each peptide was analysed by reverse-phase high-performance liquid chromatography (RP-HPLC). A Waters 717 Plus injector, a Waters 996 photodiode-array detector and a Waters 600 pump system were used. The stationary phase consisted of a reverse-phase O18 silica column (RP-18) with a particle size of 5 μm, 12.5 cm in length and 0.8 cm in diameter (LiChrospher®100, Merck). The mobile phase consisted of an H20:CH3CN mixture. A small quantity of peptide was dissolved in H20:CH3CN (90:10) and analysed. In the first place, the peptides eluted from the column by a linear gradient of acetonitrile from 10% to 90% in water (both eluents contained 0.1% TFA, which acts as a disaggregating agent) for 30 min at a flow rate of 1 ml/min. In this way, different retention times were observed as a function of the peptides' hydrophobicity. Depending on the chromatographic profile of the peptides to be purified, it was performed isocratically or by linear gradient. In the isocratic mode, the proportion of H20:CH3CN is fixed and it was determined for each peptide. When a gradient is used, the minimum and maximum necessary amounts of water or acetonitrile for elution of the peptide was determined (FIG. 7A). In either case, the eluted peak corresponding to the peptide was detected by measuring the absorbance at 220 nm (wavelength whereat the peptide bond is detected) and at 280 nm (where aromatic amino acids are detected). Once the chromatographic profile of each synthesised peptide was determined, they were purified by the preparative RP-HPLC technique. The equipment used consisted of a Waters Delta Prep. 3000 injector and pump controller, an L-7400 (Merck) ultraviolet (UV) detector and a LiChrosorb® RP-18 column with a particle size of 7 μm, 27 cm in length and 3.5 cm in diameter (Merck). The purification led to the elimination of the truncated peptides and the potential residual components obtained from synthesis 15. The peak corresponding to the purified peptide was characterised by analytical RP-HPLC (FIG. 7B) and its identity was confirmed by MALDI-TOF (matrix-assisted laser desorption/ionisation time-of-flight) mass spectrometry (FIG. 7C). The peptides were dissolved in 5 mM of 3(N-morpholin)-propanesulfonic acid (MOPS) buffer at pH 7 and the concentration was quantified by spectrophotometry ($A_{280}$, $\xi^{280}$=5600 $M^{-1}$ $cm^{-1}$).

Biological Production of the Oligopeptides

Production of the peptides obtained on a solid support as described in the preceding section may also be performed by means of biotechnological strategies, with techniques known by those skilled in the art, using recombinant DNA methodology and the genetic transformation of organisms. A selective synthesis of a given stereoisomer, for example, the D-hexapeptide, may be obtained using a genetically transformed organism that is a large-scale producer of the peptide of interest.

Thus, in a first aspect, this invention relates to oligopeptides designed for the treatment of AIDS, which inhibit the fusogenic activity of viral glycoprotein gp41 of HIV.

As cited in this invention, the term oligopeptide refers to peptides formed by ten amino acids or less.

In a preferred embodiment, this invention relates to oligopeptides designed for the treatment of AIDS, which inhibit the fusogenic activity of viral glycoprotein gp41 of HIV, and which comprise the hexapeptides characterised in that they have SEQ ID NO: 1 or SEQ ID NO: 2.

In another preferred embodiment, this invention relates to oligopeptides designed for the treatment of AIDS, which inhibit the fusogenic activity of viral glycoprotein gp41 of HIV, where said oligopeptides are hexapeptides characterised in that they have SEQ ID NO: 1 or SEQ ID NO: 2.

A second aspect of this invention relates to the use of the oligopeptides of the invention in the preparation of a pharmaceutical composition designed for the treatment or prevention of AIDS.

A third aspect of this invention relates to the use of the hexapeptides of the invention in the preparation of a pharmaceutical composition designed for the treatment or prevention of AIDS.

A fourth aspect of this invention relates to a prophylactic treatment method for AIDS, which comprises the administration of a pharmaceutically acceptable quantity of oligopeptides designed to inhibit the fusogenic activity of viral glycoprotein gp41 of HIV to an individual at risk of suffering an HIV infection.

A preferred embodiment of this invention relates to a prophylactic treatment method for AIDS, which comprises the administration of a pharmaceutically acceptable quantity of oligopeptides designed to inhibit the fusogenic activity of viral glycoprotein gp41 of HIV to an individual at risk of suffering an HIV infection, where the oligopeptides comprise hexapeptides characterised in that they have sequences SEQ ID NO: 1 or SEQ ID NO: 2.

Another preferred embodiment of this invention relates to a prophylactic treatment method for AIDS, which comprises the administration of a pharmaceutically acceptable quantity of oligopeptides designed to inhibit the fusogenic activity of viral glycoprotein gp41 of HIV to an individual at risk of suffering an HIV infection, where the oligopeptides are hexapeptides characterised in that they have sequences SEQ ID NO: 1 or SEQ ID NO: 2.

A fifth aspect of this invention relates to the HIV Virus, characterised in that it has been treated, in vitro, with the oligopeptides of the invention that inhibit the fusogenic activity of viral glycoprotein gp41 of HIV.

A preferred embodiment of this invention relates to the HIV Virus, characterised in that it has been treated, in vitro, with the oligopeptides of the invention that inhibit the fusogenic activity of viral glycoprotein gp41 of HIV, where said oligopeptides comprise hexapeptides characterised in that they have sequences SEQ ID NO: 1 or SEQ ID NO: 2.

Another preferred embodiment of the invention relates to the HIV Virus, characterised in that it has been treated, in vitro, with the oligopeptides of the invention that inhibit the fusogenic activity of viral glycoprotein gp41 of HIV, where said oligopeptides are hexapeptides characterised in that they have sequences SEQ ID NO: 1 or SEQ ID NO: 2.

Below are listed embodiment examples of the invention, which are intended to illustrate the invention, but in no way to limit it.

EMBODIMENT EXAMPLES OF THE INVENTION

Example 1

Oligopeptide gqidev (oligopeptide identified by SEQ ID NO: 1) was synthesised as disclosed in the detailed description of the invention. It was added, at a concentration of 5 µM (micromolar), to the cell culture medium (GMEM-S supplemented with 1 mM sodium pyruvate and 0.4 mM methionine sulfoximine). HIV-1 gp120/41 protein expression cells (effector cells) were incubated with the medium supplemented with oligopeptides of the invention for 1 hour at 37° C. Subsequently, CD4-receptor expression cells, which, moreover, endogenously synthesise co-receptor CXCR4 (target cells), were added. The plates were developed after 16 hours of co-incubation. The activity of gp41 is detected by the formation of multi-nucleated cells (CTL panel) produced by the fusion of the plasma membranes. It was observed that oligopeptide gqidev (oligopeptide identified by SEQ ID NO: 1) had an inhibitory effect comparable to that of T-20 under these experimental conditions.

TABLE 1

Nomenclature of amino acids.

| Amino acid | | |
| --- | --- | --- |
| Alamine | Fmoc-Ala-OH | A (a) |
| Cysteine | Fmoc-Cys(Trt)-OH | C (c) |
| Aspartic | Fmoc-Asp(tBu)-OH | D (d) |
| Glutamic | Fmoc-Glu(tBu)-OH | E (e) |
| Phenylalanine | Fmoc-Phe-OH | F (f) |
| Glycine | Fmoc-Gly-OH | G (g) |
| Histidine | Fmoc-His(Trt)-OH | H (h) |
| Isoleucine | Fmoc-Ile-OH | I (i) |
| Lysine | Fmoc-Lys(BOC)-OH | K (k) |
| Leucine | Fmoc-Leu-OH | L (l) |
| Methionine | Fmoc-Met-OH | M (m) |
| Asparagine | Fmoc-Asn(Trt)-OH | N (n) |
| Proline | Fmoc-Pro-OH | P (p) |
| Glutamine | Fmoc-Glu(Trt)-OH | Q (q) |
| Arginine | Fmoc-Arg(Pmc)-OH | R (r) |
| Serine | Fmoc-Ser(tBu)-OH | S (s) |
| Threonine | Fmoc-Thr(tBu)-OH | T (t) |
| Valine | Fmoc-Val-OH | V (v) |
| Tryptophan | Fmoc-Trp(BOC)-OH | W (w) |
| Tyrosine | Fmoc-Tyr(tBu)-OH | Y (y) |

*Table 1. The D stereoisomers of natural amino acids are represented with lower-case letters in the one-letter code.

BIBLIOGRAPHY

1. Wild, C. T., Shugars, D. C., Greenwell, T. K., McDanal, C. B., and Matthews, D. J. (1994). Peptides corresponding to a predictive alpha-helical domain of human immunodeficiency virus type 1 gp41 are potent inhibitors of virus infection. Proc. Natl. Acad. Sci. USA 91, 9770-9774.
2. Kilby, J. M., Hopkins, S., Venetta, T. M., et al. (1998). Potent suppression of HIV-1 replication in humans by T-20, a peptide inhibitor of gp41-mediated virus entry. Nature Medicine 4, 1302-1307.
3. Schneider, S. E., Bray, B. L., Mader, C. J. et al. (2005). Development of HIV fusion inhibitors. J. Peptide Sci. 11, 744-753.
4. Doms, R. W., and Moore, J. P. (2000). HIV-1 membrane fusion: targets of opportunity. J. Cell Biol. 151, F9-F13.
5. Gallaher, W. R. (1987). Detection of a fusion peptide sequence in the transmembrane protein of the human immunodeficiency virus. Cell 50, 327-328.
6. Nieva, J. L., and Agirre, A. (2003). Are fusion peptides a good model to study viral cell fusion? Biochim. Biophys. Acta 1614, 104-115.
7. Owens, R. J., Tanner, C. C., Mulligan, M. J., Srinivas, R., and Compans, R. W. (1990). Oligopeptide inhibitors of HIV-induced syncytium formation. AIDS Res. Hum. Retroviruses 6, 1289-1296.
8. Pereira, F. B., Goñi, F. M., and Nieva, J. L. (1997). Membrane fusion induced by the HIV-1 fusion peptide: modulation by factors affecting gp41 activity and potential anti-HIV compounds. AIDS Res. Hum. Retroviruses 13, 1203-1211.

The invention claimed is:

1. An isolated peptide consisting of 10 or fewer amino acids, wherein the peptide comprises SEQ ID NO:1 or SEQ ID NO:2.

2. The peptide according to claim 1, which comprises SEQ ID NO: 1.

3. The peptide according to claim 1, which comprises SEQ ID NO: 2.

4. An isolated hexapeptide which consists of SEQ ID NO: 1 or SEQ ID NO: 2.

5. The peptide according to claim 4, which consists of SEQ ID NO: 1.

6. The peptide according to claim 4, which consists of SEQ ID NO: 2.

7. A pharmaceutical composition comprising the peptide according to claim 1 in an amount effective to inhibit the fusogenic activity of viral glycoprotein gp41 of an HIV virus in a subject.

8. A pharmaceutical composition comprising the hexapeptide according to claim 4 in an amount effective to inhibit the fusogenic activity of viral glycoprotein gp41 of an HIV virus in a subject.

* * * * *

```
                        SEQUENCE LISTING

<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Oligopeptide gqidev

<400> SEQUENCE: 1

Gly Gln Ile Asp Glu Val
1               5

<210> SEQ ID NO 2
<211> LENGTH: 6
<212> TYPE: PRT
<213> ORGANISM: Artificial Sequence
<220> FEATURE:
<223> OTHER INFORMATION: Oligopeptide gqidqv

<400> SEQUENCE: 2

Gly Gln Ile Asp Gln Val
1               5

<210> SEQ ID NO 3
<211> LENGTH: 6
<212> TYPE: PRT
<213> ORGANISM: Artificial Sequence
<220> FEATURE:
<223> OTHER INFORMATION: Oligopeptide gpidqv

<400> SEQUENCE: 3

Gly Pro Ile Asp Gln Val
1               5
```